United States Patent [19]

Coffen et al.

[11] Patent Number: 5,037,747
[45] Date of Patent: Aug. 6, 1991

[54] PRODUCTION OF BENZOPYRAN-2-CARBOXYLIC ACIDS AND ESTERS BY ENZYMATIC HYDROLYSIS

[75] Inventors: David L. Coffen, Glenridge; Panayiotis Kalaritis, New Providence; John J. Partridge, Upper Montclair, all of N.J.

[73] Assignee: Hoffmann-La Roche Inc., Nutley, N.J.

[21] Appl. No.: 148,469

[22] Filed: Jan. 26, 1988

[51] Int. Cl.[5] .................. C12P 17/06; C07C 67/00; C07C 51/00
[52] U.S. Cl. ............................ 435/125; 435/280; 435/874
[58] Field of Search ................ 435/125, 280, 874

[56] References Cited

U.S. PATENT DOCUMENTS

| | | | |
|---|---|---|---|
| 4,022,664 | 5/1977 | Kawamura et al. | 435/280 |
| 4,668,628 | 5/1987 | Dahod et al. | 435/135 |
| 4,933,282 | 6/1990 | Hasegawa et al. | 435/135 |
| 4,933,290 | 6/1990 | Cesti et al. | 435/280 |

FOREIGN PATENT DOCUMENTS 57-94295  6/1982  Japan .

OTHER PUBLICATIONS

Kato et al., Tetrahedron Letters, vol. 28, No. 12, pp. 1303–1306 (1987).
Gu et al., Tetrahedron Letters, vol. 27, No. 43, pp. 5203–5206 (1986).
Dernoncour et al., Tetrahedron Letters, vol. 28, No. 40, pp. 4661–4664 (1987).
Kitazume et al., J. Org. Chem., vol. 51, pp. 1003–1004 (1986).
Xie et al., J. Chem. Soc., Chem. Commun., pp. 838–839 (1987).
Cambou and Klibanov, Applied Biochemistry and Biothechnology, vol. 9, pp. 255–260 (1984).
J. Physiol., 30, 253 (1904).
J. Amer. Chem. Soc., 77, 4271 (1955).
J. Amer. Chem. Soc., 83, 4228 (1961).
Technical Bulletin Amano Int'l Enzyme Co.
Iriuchijima et al., "Asymmetric Hydrolysis of ($\pm$)-$\alpha$-Substituted Carboxylic Acid Esters With Microorganisms", Agric. Biol. Chem. V45(6), 1389–1392, 1981.

Primary Examiner—Elizabeth C. Weimar
Assistant Examiner—Gail Poulos
Attorney, Agent, or Firm—George M. Gould; Bernard S. Leon; Alan P. Kass

[57] ABSTRACT

Enantiomerically pure (2R)-hydroxy-substituted benzopyran-2-carboxylic acid esters and (2S)-hydroxy-substituted benzopyran-2-carboxylic acids, are prepared by the Pseudomonas lipase-catalyzed selective hydrolysis of racemic (2RS)-hydroxy-substituted benzopyran-2-carboxylic acid esters in solution or suspension in an aqueous or aqueous/organic medium, at a pH of from about 5 to about 10.

13 Claims, No Drawings

PRODUCTION OF BENZOPYRAN-2-CARBOXYLIC ACIDS AND ESTERS BY ENZYMATIC HYDROLYSIS

The specificity of certain microorganisms or of certain enzymes derived from microorganisms enables their potential use for the preparation of enantiomerically pure intermediates from racemic mixtures. The desired enantiomeric molecule can then be transformed into the target compound. Microorganism or enzyme-catalyzed resolution of isomers offers an attractive alternative to more traditional and costly methods, such as chemical resolution and high preformancce liquid chromatography of diastereomeric derivatives.

Kato et al. have reported that a known bacterium, *Corynbacterium equi* IFO 3730, has the ability to hydrolyze various esters enantioselectively (*Tetrahedron Letters*, Vol. 28, No. 12, 1987, pages 1303–1306). In their study, the microorganism was applied to the asymmetric hydrolysis of 2-benzyloxy substituted alkane- and arylalkane carboxylic acid esters, using a suspension of grown cells of *C. equi* and a prolonged (e.g., 24 hours) fermentation process. Unreacted lower alkyl esters were recovered in the optically active S-form in high enantiomeric excess (over 99% e.e.). It was also found that changing the alkyl or alkenyl moiety of the substrate with a phenylmethyl group caused a reversal of stereoselectivity, resulting in recovery of the optically active R-form, also in high enantiomeric excess.

Kitazume et al. have described a procedure for the asymmetric hydrolysis of 2-fluoro-2-methylmalonic acid diesters with pig liver esterase, giving the optically active (−)-2-fluoro-2-methylmalonic acid monoesters but with low enantiomeric excess. Also reported were the microbial hydrolysis of 2-fluoro-2-substituted malonic acid diesters with both esterase and cellulase to give the optically active (+)- or (−)-2-fluoro-2-substituted malonic acid monoesters (*J. Org. Chem.* 51, 1986, pages 1003–1006).

Gu et al. have reported that optically active 3-benzoylthio-2-methylpropionic acids can be prepared through the microbial lipase-catalyzed enantioselective hydrolysis of their corresponding esters. Enantioselectivity to the desired sterochemically preferred S-isomer was poor with all lipases tried, necessitating structural changes in the aroylthio moiety of the substrate compound to achieve higher stereoselectivity. In particular, introduction of methoxy groups into the phenyl ring at the 3 and 5 positions resulted in improved stereospecificity using the lipase of *Mucor meihei* (*Tetrahedron Letters*, Vol. 27, No. 43, 1986, pages 5203–5206).

Iuchijima et al. have described a process for the production of optically active 2-chloro- and 2-bromo-substituted alkyl esters and acids by the asymmetric hydrolysis of racemic mixtures of the ester, using the microorganisms Rizopus, Mucor, Aspergillus, Candida, Pseudomonas, Alcaligenes, Achromobacter and Bacillus, or enzymes derived from them. Published Japan Patent Application (Kokai) No. 57-94, 295 (1982).

Also reported in the literature have been the Candida lipase-catalyzed enantioselective hydrolysis of racemic octyl 2-chloropropionate to the R-form of 2-chloropropionic acid (Cambou and Klibanov, *Appl. Biochem. Biotech.* 9, 1984, p. 255).

U.S. Pat. No. 4,668,628 (Dahod et al.) discloses a process for enzymatically resolving racemic mixtures of partially water-soluble esters, which involves contacting the racemic mixture with a Candida lipase enzyme to enzymatically hydrolyze it. A specific example is the Candida lipase catalyzed hydrolysis of D,L-methyl-2-chloropropionate.

A disadvantage of lipase-catalyzed kinetic resolutions in particular is that the specificity of the enzyme for a given substrate often cannot be anticipated in advance, since there is no useful model available for predicting the stereochemical outcome of a lipase-catalyzed kinetic resolution of a potential substrate.

SUMMARY OF THE INVENTION

This invention provides a novel process for obtaining optically pure hydroxy-substituted benzopyran-2-carboxylic acids and esters by the enzymatic kinetic resolution of racemic (2RS)-3,4-dihydro-7-hydroxy-2H-1-benzopyran-2-alkanoic acid esters, using a bacterial lipase enzyme as the resolving agent.

More specifically, it has been discovered that this process can be used to selectively convert the compound of formula I, below, into a mixture of the compounds of formulas IA and II, which can thereafter be separated to yield the desired 2R isomer of formula IA and the desired 2S isomer of formula II.

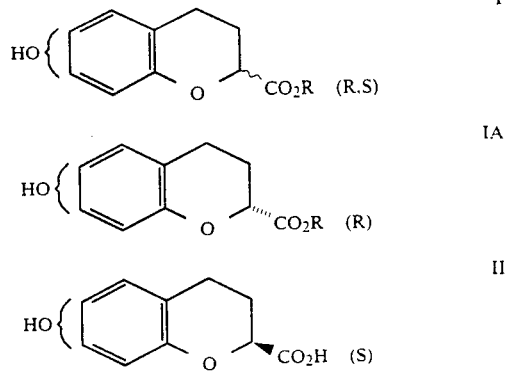

in which R is alkyl, aryl or aralkyl, each of which can be substituted or unsubstituted.

DETAILED DESCRIPTION OF THE INVENTION

As used throughout this disclosure, the term "alkyl" includes both straight and branched chain alkyl groups, preferably having from 1 to 8 carbon atoms, such as methyl, ethyl, propyl, isopropyl, butyl, and so forth.

As also used herein, the term "aryl" refers to mononuclear aromatic hydrocarbon groups such as phenyl, which can be unsubstituted or substituted in one or more positions, and polynuclear aryl groups such as naphthyl, anthryl, phenanthryl, and so forth, which can be unsubstituted or substituted with one or more groups. The preferred aryl groups are mononuclear aryl, especially phenyl.

The term "aralkyl" refers to straight and branched chain alkyl groups, preferably of from 1 to 8 carbon atoms, terminating in an aryl group as described above.

Each of the above mentioned alkyl, aryl or aralkyl groups can optionally the substituted in one or more positions with a variety of substituents, such as halogen, alkoxy, aryloxy, thioalkoxy, thioaryloxy, and alkyl, preferably halogen (chloro, bromo, fluoro or iodo).

In the depiction of the compounds given throughout this description, a thickened taper line (▲) indicates a substituent which is in the beta-orientation (above the plane of the molecule or page), a broken line ($\equiv$) indicates a substituent which is in the alpha-orientation (below the plane of the molecule or page), and a wavy line ($\{$) indicates a substituent which is in either the alpha- or beta-orientation or mixtures of these isomers.

In accordance with this invention, it has been found that when the racemic mixture of formula I is subjected to enzymatic hydrolysis utilizing a bacterial lipase enzyme, derived from a Pseudomonas species, the 2S-enantiomer of formula I form is selectivity hydrolyzed to produce the 2S-enantiomer of formula II. The enzymatic kinetic resolution can also be utilized to convert a racemic mixture of formula I to the 2R-enantiomer of formula IA.

This enzymatic hydrolysis thus produces the 2R-enantiomer of formula IA in admixture with the 2S-enantiomer of formula II. These compounds can be thereafter easily separated by conventional techniques.

In conducting the enzymatic reaction, the compound of formula I is dissolved or, if necessary, suspended in an aqueous medium or a mixed aqueous/organic solvent medium. In suspending the compound of formula I in an aqueous medium, emulsifying agents may be used to enhance or to facilitate the emulsification, and conventional emulsifying agents may be utilized for this purpose.

The organic solvent or solvents employed in the mixed aqueous/organic solvent system can be completely water miscible, for example, methanol and acetone, or only partially water miscible, for example, acetonitrile, tetrahydrofuran, ether and toluene. Typically, the water is employed in a major amount and the organic solvent is utilized in a minor amount, by volume. Most usually, the volume ratio of water to organic solvent is in the range from about 1:1 to about 10:1, preferably from about 3:1 to about 9:1.

The enzymatic hydrolysis is carried out at a pH of from about 5 to about 10, preferably at a pH of from about 7 to about 9. Any conventional method of maintaining the pH of the reaction mixture at the aforementioned pH can be employed. Among the preferred methods are the use of buffers or automatic titration.

In carrying out this enzymatic hydrolysis, the racemic mixture of formula I dissolved or otherwise dispersed in an aqueous medium is treated with a bacterial lipase enzyme. It is generally preferred to utilize the enzyme in a catalytically effective amount. As would be recognized, to achieve best results the choice of a particular catalytically effective amount of enzyme will depend upon factors within the control of one skilled in the art. These factors include the amount of starting material, the enzyme source, the unit activity of the enzyme, the purity of the enzyme, and so forth. An excess of a catalytically effective amount of the bacterial lipase enzyme can be used, but no additional beneficial results are obtained through the use of large excesses of enzyme.

As stated above, the enzymatic hydrolysis of the compound of formula I produces the compound of formula IA in admixture with the compound of formula II. These compounds can be easily separated once the enzymatic hydrolysis is stopped, by immediate extraction of the reaction medium with a suitable organic solvent. Any conventional method of separation can be utilized to isolate the compound of formula IA form the compound of formula II. Among the conventional means for separating these two compounds are included extraction and distillation.

The compounds obtained by the method of this invention are useful as intermediates for the preparation of compounds for the treatment of allergies and inflammatory conditions such as contact dermatitis, psoriasis and inflammatory bowel disease. Such anti-allergic and anti-inflammatory compounds are also variously known as leukotriene antagonists, SRS-A (substance of anaphylaxis) antagonists and mediators of the 5-lipoxygenase pathway. Processes for their preparation from compounds such as involved here are described in the patent literature, for instance, published European Patent Application No. 129906, dated June 24, 1983 [Chemical Abstracts, 103, 6223 S (1985)].

The invention is further illustrated in the Examples which follow, which are not intended to be limiting.

In the following Examples, the enantiomeric excess (% e.e.) of the R- and S- esters were determined by HPLC analysis on a 25 cm × 4.6 cm covalently bonded (R)-phenylglycine column (Regis Chromatography Co.). This column was eluted with 10% EtOH-heptane using a flow rate of 1 mL/min. The eluted fractions were detected by a UV detector at 254 nm. For a description of the column and known separations, see W. H. Pirkle et al., *J. Org. Chem.*, 46, 1981, page 4988. The carboxylic acids were analyzed upon conversion to the corresponding esters.

EXAMPLE 1

Enzymatic Kinetic Resolution of Racemic 3,4-Dihydro-7-Hydroxy-2H-1-Benzopyran-2-Carboxylic Acid Ethyl Ester A 250 mL 3-necked, round-bottomed flask equipped with a mechanical stirrer, a pH electrode connected to a pH control unit and an addition tube connected to a peristaltic pump, was charged with 60 mL of deionized water, 15 mL of 0.05M phosphate buffer (pH 7.0) and 2.2 g racemic 3,4-dihydro-7-hydroxy-2H-1-benzopyran-2-carboxylic acid ethyl ester dissolved in 7.5 mL of tetrahydrofuran. The pH was adjusted to 8.0 with 0.1N aqueous hydroxide solution, and 0.4 g of Pseudomonas lipase enzyme (P-30, Amano International Enzyme Co., Inc., Troy, Va.) was added while the mixture was stirred at a fast rate. The reaction flask was stoppered to avoid loss of the co-solvent by evaporation and the stirring was continued at the same rate. The pH was maintained at 8.0 by adding 0.1N aqueous sodium hydroxide solution via the peristaltic pump. The reaction was discontinued when 55 mL of 0.1N aqueous sodium hydroxide had been consumed (at about the 10 hour mark) and the tetrahydrofuran was removed by evaporation at 35° C. under 10 mm Hg of vacuum. The remaining mixture was extracted 3 times with 50 mL (for a total of 150 mL) of ethyl acetate. The combined organic layers were washed with 50 mL of saturated aqueous sodium bicarbonate and dried over anhydrous sodium sulfate. The solution was filtered and concentrated at 40° C. under 10 mm Hg of vacuum, to obtain 1.0 g (45% yield, 100% of theory) of (R)-3,4-dihydro-7-hydroxy-2H-1-benzopyran-2-carboxylic acid ethyl ester as an off-white solid; m.p. 77°–78° C., $(\alpha)_D^{25}$ −20.2° (c 1.0, CHCl$_3$), 99.6% e.e.

The aqueous layer was acidified to pH 1.0 with concentrated hydrochloric acid and extracted twice with 50 mL (for a total of 100 mL) of ethyl acetate. The combined organic layers were dried over anhydrous sodium sulphate, filtered and concentrated at 40° C. under 10 mm Hg of vacuum, to give 0.96 g (50%, 90% of theory) of (S)-3,4-dihydro-7-hydroxy-2H-1-benzopyran-2-carboxylic acid as an off-white solid; m.p. 156.5°–158.5° C., $(\alpha)_D^{25}$ −9.2° (c 1.0, MeOH), 75% e.e.

EXAMPLE 2

Preparation of (S)-3,4-Dihydro-7-Hydroxy-2H-1-Benzopyran-2-Carboxylic Acid Ethyl Ester by Enzymatic Hydrolysis A 5 L three-necked flask equipped with a mechanical stirrer, a pH electrode connected to a pH control unit and an addition tube connected to a peristaltic pump, was charged with 2.73 L of deionized water, 682 mL of 0.05M phosphate buffer (pH 7.0) and a solution of 100.0 g (0.45 mol) of racemic-3,4-dihydro-7-hydroxy-2H-1-benzopyran-2-carboxylic acid ethyl ester in 340 mL of tetrahydrofuran. The pH was adjusted to 8 with adequate 1.0N aqueous sodium hydroxide solution, and 9.0 g of Pseudomonas lipase enzyme (P-30, Amano International) was added to the mixture. The hydrolysis was allowed to proceed while stirring at a fast rate and keeping the pH at 8 by adding adequate 1.0N aqueous sodium hydroxide solution via the pump. The hydrolysis was stopped when 40% of the base has been consumed. The tetrahydrofuran in the reaction mixture was removed at 40° C. (10 mm Hg of vacuum) and the aqueous phase was extracted 3×1.0 L=3.0 L of ethyl acetate. The combined organic extracts were washed successively with 500 mL of saturated aqueous sodium bicarbonate solution and 500 mL of brine, then dried over anhydrous sodium sulfate. The drying agent was removed by filtration and the solvent was removed at 35° C. (10 mm Hg) to give 35.1 g (35% yield; 86% of theory) of (R)-3,4-dihydro-7-hydroxy-2H-1-benzopyran-2-carboxylic acid, ethyl ester as a beige solid, m.p. 77°–78° C.; $(\alpha)_D^{22}$ −18.8° (c 1.0, CHCl$_3$), 93.5% e.e.

The combined aqueous layers were acidified to pH=1.0 with 100 mL of concentrated hydrochloric acid and extracted with 3×1.0 L=3.0 L of ethyl acetate. The combined organic layers were washed with 500 mL of brine and dried over anhydrous sodium sulfate. After filtration the solvent was removed at 40° C. (10 mm Hg) to give 51.6 g of crude (S)-3,4-dihydro-7-hydroxy-2H-1-benzopyran-2-carboxylic acid as a gummy solid. A small amount of this material (1.6 g) was purified by trituration with chloroform and dried overnight at 40°–45° C. (0.5 mm Hg), m.p. 156.5°–158.5° C.; $(\alpha)_D^{22}$ −12.1° C. (c 1.0, CH$_3$OH). The remainder of the crude carboxylic acid was subsequently esterified in 1.0 L of ethanol containing 1.0 mL of concentrated sulfuric acid which was heated at reflux for 2 hours under argon. Most of the solvent was distilled atmospherically and the residue was poured into 500 mL of deionized water. The mixture was extracted with 3×100 mL=300 mL of ethyl acetate. The combined organic layers were washed successively with 200 mL of saturated aqueous sodium bicarbonate solution, 200 mL of deionized water and dried over anhydrous sodium sulfate. After filtration the solvent was removed at 40° C. (10 mm Hg) and the solids were further dried at 40°–45° C. (0.5 mm Hg) overnight. The optically active (S)-3,4-dihydro-7-hydroxy-2H-1-benzopyran-2-carboxylic acid ethyl ester weighed 30.0 g (26% yield; 50% of theory), m.p. 77°–79° C.; $(\alpha)_D^{22}$ +18.1° C. (c 1.0, CHCl$_3$); 83% e.e.

This ester was then resubmitted to enzymatic hydrolysis with Pseudomonas lipase (P-30, Amano International) to enhance its enantiomeric purity. A 3 L three-necked flask equipped as described above was charged with 775 mL of deionized water, 194 mL of 0.05M phosphate buffer (pH 7.0) and 28.4 g (0.128 mol) of the above ester in 96 mL of tetrahydrofuran. The pH was adjusted to 8 with adequate 1.0N aqueous sodium hydroxide solution and 2.6 g of Pseudomonas lipase enzyme (P-30 Amano) was added to the mixture. The hydrolysis was allowed to proceed to 70% conversion over a 7 hour period while stirring at a fast rate and maintaining the pH at 8. The tetrahydrofuran was removed from the reaction mixture at 40° C. (10 mm Hg) and the aqueous phase was extracted with 3×250 mL=750 mL of ethyl acetate. The combined organic layers were washed successively with 250 mL of saturated aqueous sodium bicarbonate solution and 250 mL of deionized water. The organic phase was dried over anhydrous sodium sulfate, filtered and concentrated at 40° C. (10 mm Hg) to give 6.7 g of nearly racemic 3,4-dihydro-7-hydroxy-2H-benzopyran-2-carboxylic acid ethyl ester. The aqueous layers were acidified to pH=1 with 33 mL of concentrated hydrochloric acid and extracted with 3×250 mL=750 mL of ethyl acetate. The combined organic layers were washed with 250 mL of brine and dried over anhydrous sodium sulfate. After filtration, the solvent was removed at 40° C. (10 mm Hg) to give 20.4 g of (S)-3,4-dihydro-7-hydroxy-2H-1-benzopyran-2-carboxylic acid, 95.5% e.e. This material was esterified as described above to give 21.6 g (76% yield) of (S)-3,4-dihydro-7-hydroxy-2H-1-benzopyran-2-carboxylic acid, ethyl ester as a beige solid, m.p. 77°–79° C.; $(\alpha)_D^{22}$ +19.1° C. (c 1.0, CHCl$_3$); 95.5% e.e.

We claim:

1. A process for resolving a racemic mixture comprising, treating a racemic 2RS ester selected from the group consisting of

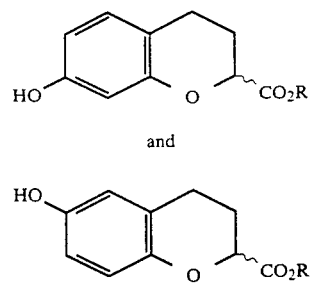

and wherein R is alkyl, aryl or aralkyl, each of which can be substituted or unsubstituted with Pseudomonas lipase P-30 enzyme in an aqueous or aqueous/organic reaction medium, said treatment carried out while maintaining the pH of the medium from about 5 to about 10, resolving said 2RS ester.

2. The process of claim 1, wherein the reaction medium is maintained at a pH of from about 7 to about 9.

3. The process of claim 1, wherein the reaction medium is composed of water and tetrahydrofuran.

4. The process of claim 3, wherein the reaction medium is composed of water and tetrahydrofuran is a range from about 3:1 to 9:1.

5. The process of claim 1, wherein R is lower alkyl.

6. The process of claim 5, wherein R is methyl or ethyl.

7. The process of claim 1 wherein said racemic 2RS ester is resolved into a 2R ester selected from the group consisting of

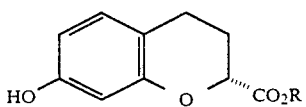

and

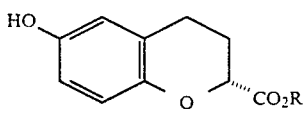

and a 2S carboxylic acid selected from the group consisting of

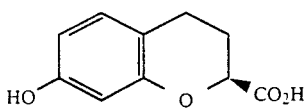

and

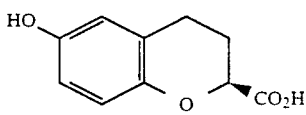

8. The process of claim 7 further comprising separating said 2R ester from said 2S carboxylic acid.

9. The process of claim 1, for producing a compound of the formula

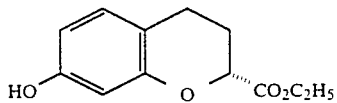

and a compound of the formula

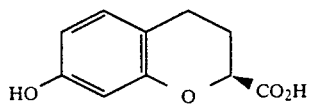

10. A process for producing 2R ester comprising, treating a racemic 2RS ester mixture selected from the group consisting of

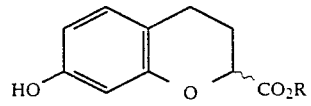

and

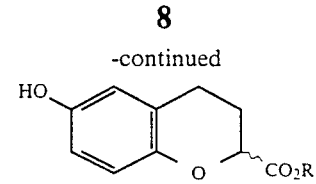

wherein R is alkyl, aryl or aralkyl, each of which can be substituted or unsubstituted with Pseudomonas lipase P-30 enzyme in an aqueous or aqueous/organic reaction medium, the treatment being carried out while maintaining the pH of the medium from about 5 to about 10, resolving said 2RS ester mixture.

11. The process of claim 10 wherein said 2R ester is selected from the group consisting of

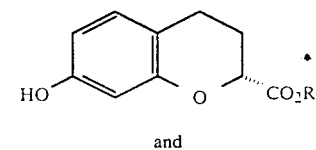

and

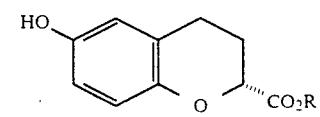

12. A process for producing 2S carboxylic acids comprising, treating a racemic 2RS ester mixture selected from the group consisting of

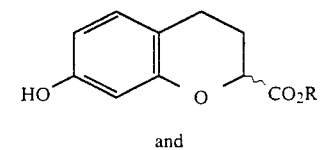

and

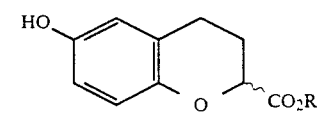

wherein R is alkyl, anyl or aralkyl, each of which can be substituted or unsubstituted with Pseudomonas lipase P-30 enzyme in an aqueous or aqueous/organic medium, the treatment being carried out while maintaining the pH of the medium from about 5 to about 10, resolving the 2RS ester mixture.

13. The process of claim 12 wherein said 2S carboxylic acid is selected from the group consisting of

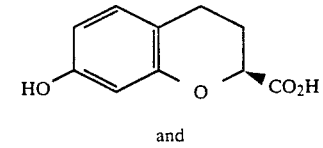

and

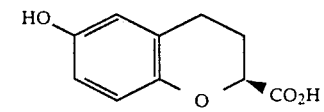

* * * * *